(12) United States Patent
Ochs et al.

(10) Patent No.: US 9,687,159 B2
(45) Date of Patent: Jun. 27, 2017

(54) SYSTEMS AND METHODS FOR DETERMINING PHYSIOLOGICAL INFORMATION BY IDENTIFYING FIDUCIAL POINTS IN A PHYSIOLOGICAL SIGNAL

(71) Applicant: Covidien LP, Mansfield, MA (US)

(72) Inventors: James Ochs, Seattle, WA (US); Scott McGonigle, Edinburgh (GB)

(73) Assignee: Covidien LP, Mansfield, MA (US)

( * ) Notice: Subject to any disclaimer, the term of this patent is extended or adjusted under 35 U.S.C. 154(b) by 841 days.

(21) Appl. No.: 13/778,999

(22) Filed: Feb. 27, 2013

(65) Prior Publication Data

US 2014/0243628 A1 Aug. 28, 2014

(51) Int. Cl.
| A61B 5/1455 | (2006.01) |
| A61B 5/0205 | (2006.01) |
| A61B 5/024 | (2006.01) |
| A61B 5/1495 | (2006.01) |
| A61B 5/00 | (2006.01) |

(52) U.S. Cl.
CPC ........ *A61B 5/0205* (2013.01); *A61B 5/02416* (2013.01); *A61B 5/14551* (2013.01); *A61B 5/7239* (2013.01); *A61B 5/1495* (2013.01); *A61B 5/7225* (2013.01); *A61B 2562/085* (2013.01)

(58) Field of Classification Search
None
See application file for complete search history.

(56) References Cited

U.S. PATENT DOCUMENTS

| 5,188,108 A | 2/1993 | Secker |
| 5,285,783 A | 2/1994 | Secker |
| 5,285,784 A | 2/1994 | Seeker |
| 5,368,026 A | 11/1994 | Swedlow et al. |
| 5,398,682 A | 3/1995 | Lynn |
| 5,558,096 A | 9/1996 | Palatnik |

(Continued)

FOREIGN PATENT DOCUMENTS

| EP | 0072601 A1 | 2/1983 |
| EP | 1344488 A2 | 9/2003 |

(Continued)

OTHER PUBLICATIONS

Stagg and Gennser, "Electronic analysis of foetal breathing movements: A practical application of phase-locked- loop principles," Journal of Med. Eng. and Tech., Sep. 1978, vol. 2, No. 5, pp. 246-249.

(Continued)

*Primary Examiner* — Eric Winakur
*Assistant Examiner* — Marjan Fardanesh
(74) *Attorney, Agent, or Firm* — Shvarts & Leiz LLP

(57) ABSTRACT

A patient monitoring system may generate a derivative signal from a physiological signal. The derivative signal may be filtered based on a pulse rate estimate associated with the physiological signal. A plurality of crossing points may be determined for the filtered derivative signal and translated to the derivative signal. A plurality of fiducial points may be determined for the derivative signal based on the plurality of crossing points. The plurality of fiducial points may be utilized to determine physiological information from the physiological signal.

11 Claims, 7 Drawing Sheets

(56) References Cited

U.S. PATENT DOCUMENTS

| | | |
|---|---|---|
| 5,584,295 A | 12/1996 | Muller et al. |
| 5,588,425 A | 12/1996 | Sackner et al. |
| 5,605,151 A | 2/1997 | Lynn |
| 5,862,805 A | 1/1999 | Nitzan |
| 5,865,736 A | 2/1999 | Baker, Jr. et al. |
| 5,891,023 A | 4/1999 | Lynn |
| 6,002,952 A | 12/1999 | Diab et al. |
| 6,035,223 A | 3/2000 | Baker |
| 6,081,742 A | 6/2000 | Amano et al. |
| 6,095,984 A | 8/2000 | Amano et al. |
| 6,129,675 A | 10/2000 | Jay |
| 6,135,966 A | 10/2000 | Ko |
| 6,178,261 B1 | 1/2001 | Williams et al. |
| 6,223,064 B1 | 4/2001 | Lynn et al. |
| 6,229,856 B1 | 5/2001 | Diab et al. |
| 6,238,351 B1 | 5/2001 | Orr et al. |
| 6,325,761 B1 | 12/2001 | Jay |
| 6,331,162 B1* | 12/2001 | Mitchell ............ 600/485 |
| 6,334,065 B1 | 12/2001 | Al-Ali et al. |
| 6,342,039 B1 | 1/2002 | Lynn et al. |
| 6,350,242 B1 | 2/2002 | Doten et al. |
| 6,405,076 B1 | 6/2002 | Taylor et al. |
| 6,463,311 B1 | 10/2002 | Diab |
| 6,506,153 B1 | 1/2003 | Littek et al. |
| 6,561,986 B2 | 5/2003 | Baura et al. |
| 6,564,077 B2 | 5/2003 | Mortara |
| 6,606,511 B1 | 8/2003 | Al-Ali et al. |
| 6,609,016 B1 | 8/2003 | Lynn |
| 6,684,090 B2 | 1/2004 | Al-Ali et al. |
| 6,694,178 B1 | 2/2004 | Soula et al. |
| 6,702,752 B2 | 3/2004 | Dekker |
| 6,709,402 B2 | 3/2004 | Dekker |
| 6,748,252 B2 | 6/2004 | Lynn et al. |
| 6,754,516 B2 | 6/2004 | Mannheimer |
| 6,760,608 B2 | 7/2004 | Lynn |
| 6,783,498 B2 | 8/2004 | Sackner et al. |
| 6,816,741 B2 | 11/2004 | Diab |
| 6,839,581 B1 | 1/2005 | El Solh et al. |
| 6,896,661 B2 | 5/2005 | Dekker |
| 6,905,470 B2 | 6/2005 | Lee et al. |
| 6,925,324 B2 | 8/2005 | Shusterman |
| 6,931,269 B2 | 8/2005 | Terry |
| 6,966,878 B2 | 11/2005 | Schoisswohl et al. |
| 6,970,792 B1 | 11/2005 | Diab |
| 6,980,679 B2 | 12/2005 | Jeung et al. |
| 7,020,507 B2 | 3/2006 | Scharf et al. |
| 7,035,679 B2 | 4/2006 | Addison et al. |
| 7,043,293 B1 | 5/2006 | Baura |
| 7,044,918 B2 | 5/2006 | Diab |
| 7,070,566 B2 | 7/2006 | Medero et al. |
| 7,079,888 B2 | 7/2006 | Oung et al. |
| 7,147,601 B2 | 12/2006 | Marks et al. |
| 7,177,682 B2 | 2/2007 | Lovett |
| 7,190,261 B2 | 3/2007 | Al-Ali |
| 7,215,986 B2 | 5/2007 | Diab et al. |
| 7,218,966 B2 | 5/2007 | Haefner |
| 7,254,425 B2 | 8/2007 | Lowery et al. |
| 7,283,870 B2 | 10/2007 | Kaiser et al. |
| 7,336,982 B2 | 2/2008 | Yoo |
| 7,355,512 B1 | 4/2008 | Al-Ali |
| 7,367,339 B2 | 5/2008 | Hickle |
| 7,367,949 B2 | 5/2008 | Korhonen et al. |
| 7,398,115 B2 | 7/2008 | Lynn |
| 7,403,806 B2 | 7/2008 | Norris |
| 7,407,486 B2 | 8/2008 | Huiku et al. |
| 7,415,297 B2 | 8/2008 | Al-Ali et al. |
| 7,438,683 B2 | 10/2008 | Al-Ali et al. |
| 7,440,787 B2 | 10/2008 | Diab |
| 7,470,235 B2 | 12/2008 | Moriya et al. |
| 7,485,095 B2 | 2/2009 | Shusterman |
| 7,496,393 B2 | 2/2009 | Diab et al. |
| 7,499,835 B2 | 3/2009 | Weber et al. |
| 7,523,011 B2 | 4/2009 | Akiyama et al. |
| 7,561,912 B2 | 7/2009 | Schatz et al. |
| 7,610,324 B2 | 10/2009 | Troyansky et al. |
| 7,690,378 B1 | 4/2010 | Turcott |
| 7,801,591 B1 | 9/2010 | Shusterman |
| 7,869,980 B2 | 1/2011 | Casler et al. |
| 7,894,868 B2 | 2/2011 | Al-Ali et al. |
| 7,899,507 B2 | 3/2011 | Al-Ali et al. |
| 7,976,472 B2 | 7/2011 | Kiani |
| 7,988,637 B2 | 8/2011 | Diab |
| 8,019,400 B2 | 9/2011 | Diab et al. |
| 8,046,040 B2 | 10/2011 | Al-Ali et al. |
| 8,130,105 B2 | 3/2012 | Al-Ali et al. |
| 8,203,438 B2 | 6/2012 | Kiani et al. |
| 8,275,553 B2 | 9/2012 | Amundson et al. |
| 8,364,225 B2 | 1/2013 | Addison et al. |
| 2002/0117173 A1 | 8/2002 | Lynn et al. |
| 2003/0036685 A1 | 2/2003 | Goodman |
| 2003/0158466 A1 | 8/2003 | Lynn |
| 2003/0163054 A1 | 8/2003 | Dekker |
| 2004/0015091 A1 | 1/2004 | Greenwald et al. |
| 2005/0004479 A1 | 1/2005 | Townsend et al. |
| 2005/0022606 A1 | 2/2005 | Partin et al. |
| 2005/0027205 A1 | 2/2005 | Tarassenko et al. |
| 2005/0049470 A1 | 3/2005 | Terry |
| 2005/0070774 A1 | 3/2005 | Addison et al. |
| 2005/0222502 A1 | 10/2005 | Cooper |
| 2005/0222503 A1 | 10/2005 | Dunlop et al. |
| 2006/0122476 A1 | 6/2006 | Van Slyke |
| 2006/0192667 A1 | 8/2006 | Al-Ali |
| 2006/0211930 A1 | 9/2006 | Scharf et al. |
| 2006/0217614 A1 | 9/2006 | Takala et al. |
| 2006/0217615 A1* | 9/2006 | Huiku .............. A61B 5/08 600/484 |
| 2006/0258921 A1 | 11/2006 | Addison et al. |
| 2007/0004977 A1 | 1/2007 | Norris |
| 2007/0010723 A1 | 1/2007 | Uutela et al. |
| 2007/0073120 A1 | 3/2007 | Li et al. |
| 2007/0073124 A1 | 3/2007 | Li et al. |
| 2007/0129636 A1 | 6/2007 | Friedman et al. |
| 2007/0149890 A1 | 6/2007 | Li et al. |
| 2007/0179369 A1 | 8/2007 | Baker |
| 2007/0213619 A1 | 9/2007 | Linder |
| 2007/0213621 A1 | 9/2007 | Reisfeld et al. |
| 2007/0255146 A1 | 11/2007 | Andrews et al. |
| 2007/0293896 A1 | 12/2007 | Haefner |
| 2008/0077022 A1 | 3/2008 | Baker |
| 2008/0167540 A1 | 7/2008 | Korhonen et al. |
| 2008/0200775 A1 | 8/2008 | Lynn |
| 2009/0247837 A1 | 10/2009 | Ochs et al. |
| 2009/0326349 A1 | 12/2009 | McGonigle |
| 2009/0326395 A1 | 12/2009 | Watson |
| 2009/0326831 A1 | 12/2009 | McGonigle et al. |
| 2010/0113904 A1 | 5/2010 | Batchelder et al. |
| 2010/0113908 A1 | 5/2010 | Vargas et al. |
| 2010/0113909 A1 | 5/2010 | Batchelder et al. |
| 2010/0286495 A1 | 11/2010 | McGonigle |
| 2011/0066062 A1 | 3/2011 | Banet et al. |
| 2011/0071406 A1 | 3/2011 | Addison et al. |

FOREIGN PATENT DOCUMENTS

| | | |
|---|---|---|
| EP | 1507474 B1 | 2/2009 |
| WO | WO 00/21438 | 4/2000 |
| WO | WO 03/000125 A1 | 1/2003 |
| WO | WO 03/055395 A1 | 7/2003 |
| WO | WO 03/084396 A1 | 10/2003 |
| WO | WO 2004/075746 A2 | 9/2004 |
| WO | WO 2010/030238 A1 | 3/2010 |

OTHER PUBLICATIONS

Rapaport and Cousin, "New phase-lock tracking instrument for foetal breathing monitoring," Med. & Bioi. Eng. & Camp. 1982, vol. 20, pp. 1-6.

Lindberg, L.G., Ughall, H., Oberg, P.A., "Monitoring of respiratory and heart rates using a fibre-optic sensor," Medical & Biological Engineering & Computing, Sep. 1992, pp. 533-537.

\* cited by examiner

SYSTEMS AND METHODS FOR DETERMINING PHYSIOLOGICAL INFORMATION BY IDENTIFYING FIDUCIAL POINTS IN A PHYSIOLOGICAL SIGNAL

The present disclosure relates to physiological signal processing, and more particularly relates to determining physiological information based on identifying fiducial points in a physiological signal.

SUMMARY

A patient monitoring system may receive a physiological signal such as a photoplethysmograph (PPG) signal. A processed PPG signal may be generated from the PPG signal. A crossing threshold may be established for the processed PPG signal, and fiducial points may be determined based at least in part on the crossing threshold. Physiological information may be determined based at least in part on the fiducial points.

In an embodiment, the processed PPG signal may be a filtered derivative of the PPG signal. A derivative signal may be generated from the PPG signal. The derivative signal may be filtered to generate the processed PPG signal. A pass band for a band-pass filter may be based at least in part on a pulse rate estimate signal. The derivative signal may be filtered based at least in part on the pass band of the band-pass filter.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
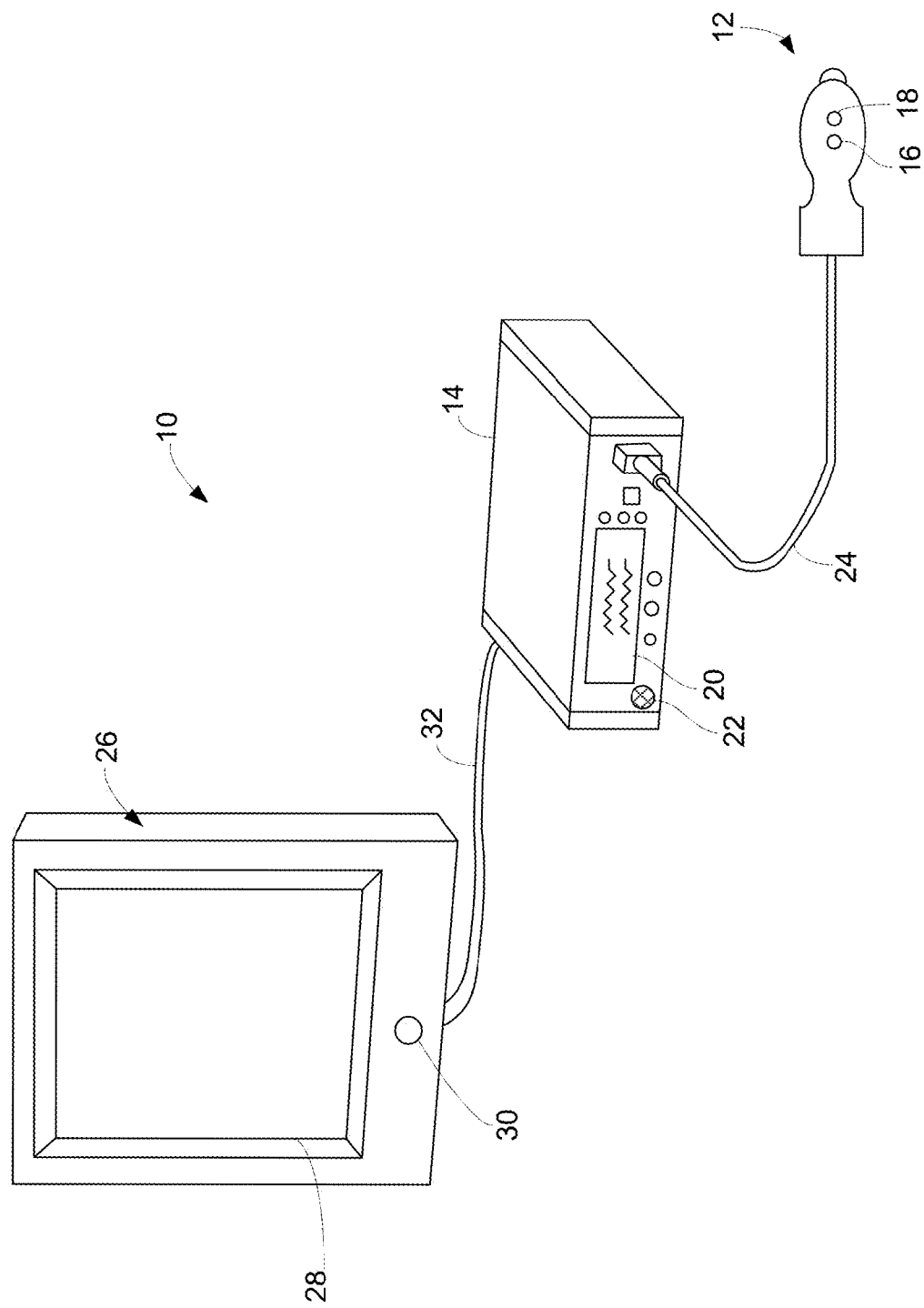
FIG. 1 shows an illustrative patient monitoring system in accordance with some embodiments of the present disclosure.

A patient monitoring system may receive a sampling window of a physiological signal such as a photoplethysmograph (PPG) signal. A first derivative signal may be generated from the PPG signal. A pulse rate estimate may be determined for the PPG signal, and the pulse rate estimate may be used to establish a pass band for a band-pass filter. The first derivate signal may be filtered by the band-pass filter to generate a filtered first derivative signal.

A power ratio may be calculated for the filtered first derivative signal and the first derivative signal to estimate the relative signal power near the pulse rate estimate. If the power ratio does not exceed a threshold, the sampling window may be ignored and no fiducial points or physiological information may be determined for the sampling window. If the power ratio exceeds a threshold, a crossing threshold may be established for the filtered first derivative signal. The crossing threshold may be based on the power of the filtered first derivative signal relative to the unfiltered signal. If the signal is noisy, the crossing threshold may be increased.

A plurality of crossing points for the filtered first derivative signal may be determine based on the crossing threshold and the pulse rate estimate. The crossing points may be translated to the first derivative signal or the original PPG signal. A plurality of maximum points of the first derivative signal may be established based on the translated points. Fiducial points may be determined based on a predetermined delay from the maximum points. In other embodiments, the delay from the maximum points may be a function of the pulse rate estimate. The delay from the maximum may increase linearly with the pulse period estimate.

For purposes of clarity, the present disclosure is written in the context of the physiological signal being a PPG signal generated by a pulse oximetry system. It will be understood that any other suitable physiological signal or any other suitable system may be used in accordance with the teachings of the present disclosure.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate.

An oximeter may include a light sensor that is placed at a site on a patient, typically a fingertip, toe, forehead or earlobe, or in the case of a neonate, across a foot. The oximeter may use a light source to pass light through blood perfused tissue and photoelectrically sense the absorption of the light in the tissue. In addition, locations that are not typically understood to be optimal for pulse oximetry serve as suitable sensor locations for the monitoring processes described herein, including any location on the body that has a strong pulsatile arterial flow. For example, additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda, t) = I_o(\lambda) \exp(-(s\beta_o(\lambda) + (1-s)\beta_r(\lambda))l(t)) \tag{1}$$

where:
$\lambda$=wavelength;
t=time;
I=intensity of light detected;
$I_0$=intensity of light transmitted;
S=oxygen saturation;
$\beta_o, \beta_r$-empirically derived absorption coefficients; and
l(t)=a combination of concentration and path length from emitter to detector as a function of time.

The traditional approach measures light absorption at two wavelengths (e.g., Red and IR), and then calculates saturation by solving for the "ratio of ratios" as follows.

1. The natural logarithm of Eq. 1 is taken ("log" will be used to represent the natural logarithm) for IR and Red to yield $$\log I = \log I_o - (s\beta_o + (1-s)\beta_r)l. \tag{2}$$

2. Eq. 2 is then differentiated with respect to time to yield $$\frac{d \log I}{dt} = -(s\beta_o + (1-s)\beta_r)\frac{dl}{dt}. \tag{3}$$

3. Eq. 3, evaluated at the Red wavelength $\lambda_R$, is divided by Eq. 3 evaluated at the IR wavelength $\lambda_{IR}$ in accordance with $$\frac{d\log I(\lambda_R)/dt}{d\log I(\lambda_{IR})dt} = \frac{s\beta_o(\lambda_R) + (1-s)\beta_r(\lambda_R)}{s\beta_o(\lambda_{IR}) + (1-s)\beta_r(\lambda_{IR})}. \tag{4}$$

4. Solving for S yields $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}. \tag{5}$$

5. Note that, in discrete time, the following approximation can be made:

$$\frac{d\log I(\lambda, t)}{dt} \simeq \log I(\lambda, t_2) - \log I(\lambda, t_1). \tag{6}$$

6. Rewriting Eq. 6 by observing that log A−log B=log(A/B) yields $$\frac{d\log I(\lambda, t)}{dt} \simeq \log\left(\frac{I(t_2, \lambda)}{I(t_1, \lambda)}\right). \tag{7}$$

7. Thus, Eq. 4 can be expressed as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R, \tag{8}$$

where R represents the "ratio of ratios."

8. Solving Eq. 4 for S using the relationship of Eq. 5 yields $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}. \tag{9}$$

9. From Eq. 8, R can be calculated using two points (e.g., PPG maximum and minimum), or a family of points. One method applies a family of points to a modified version of Eq. 8. Using the relationship $$\frac{d\log I}{dt} = \frac{\frac{dI}{dt}}{I}, \tag{10}$$

Eq. 8 becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_R)}} = \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)} = R, \tag{11}$$

which defines a cluster of points whose slope of y versus X will give R when $$x = [I(t_2, \lambda_{IR}) - I(t_1, \lambda_{IR})] I(t_1, \lambda_R), \quad (12)$$

and $$y = [I(t_2, \lambda_R) - I(t_1, \lambda_R)] I(t_1, \lambda_{IR}). \quad (13)$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

FIG. 1 is a perspective view of an embodiment of a patient monitoring system 10. System 10 may include sensor unit 12 and monitor 14. In some embodiments, sensor unit 12 may be part of an oximeter. Sensor unit 12 may include an emitter 16 for emitting light at one or more wavelengths into a patient's tissue. A detector 18 may also be provided in sensor unit 12 for detecting the light originally from emitter 16 that emanates from the patient's tissue after passing through the tissue. Any suitable physical configuration of emitter 16 and detector 18 may be used. In an embodiment, sensor unit 12 may include multiple emitters and/or detectors, which may be spaced apart. System 10 may also include one or more additional sensor units (not shown) that may take the form of any of the embodiments described herein with reference to sensor unit 12. An additional sensor unit may be the same type of sensor unit as sensor unit 12, or a different sensor unit type than sensor unit 12. Multiple sensor units may be capable of being positioned at two different locations on a subject's body; for example, a first sensor unit may be positioned on a patient's forehead, while a second sensor unit may be positioned at a patient's fingertip.

Sensor units may each detect any signal that carries information about a patient's physiological state, such as an electrocardiograph signal, arterial line measurements, or the pulsatile force exerted on the walls of an artery using, for example, oscillometric methods with a piezoelectric transducer. According to some embodiments, system 10 may include two or more sensors forming a sensor array in lieu of either or both of the sensor units. Each of the sensors of a sensor array may be a complementary metal oxide semiconductor (CMOS) sensor. Alternatively, each sensor of an array may be charged coupled device (CCD) sensor. In some embodiments, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, emitter 16 and detector 18 may be on opposite sides of a digit such as a finger or toe, in which case the light that is emanating from the tissue has passed completely through the digit. In some embodiments, emitter 16 and detector 18 may be arranged so that light from emitter 16 penetrates the tissue and is reflected by the tissue into detector 18, such as in a sensor designed to obtain pulse oximetry data from a patient's forehead.

In some embodiments, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., pulse rate, blood oxygen saturation, and respiration information) based at least in part on data relating to light emission and detection received from one or more sensor units such as sensor unit 12 and an additional sensor (not shown). In some embodiments, the calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range. In some embodiments, the system 10 includes a stand-alone monitor in communication with the monitor 14 via a cable or a wireless network link.

In some embodiments, sensor unit 12 may be communicatively coupled to monitor 14 via a cable 24. In some embodiments, a wireless transmission device (not shown) or the like may be used instead of or in addition to cable 24. Monitor 14 may include a sensor interface configured to receive physiological signals from sensor unit 12, provide signals and power to sensor unit 12, or otherwise communicate with sensor unit 12. The sensor interface may include any suitable hardware, software, or both, which may allow communication between monitor 14 and sensor unit 12.

Patient monitoring system 10 may also include display monitor 26. Monitor 14 may be in communication with display monitor 26. Display monitor 26 may be any electronic device that is capable of communicating with monitor 14 and calculating and/or displaying physiological parameters (e.g., a general purpose computer, tablet computer, smart phone, or an application-specific device). Display monitor 26 may include a display 28 and user interface 30. Display 28 may include touch screen functionality to allow a user to interface with display monitor 26 by touching display 28 and utilizing motions. User interface 30 may be any interface that allows a user to interact with display monitor 26 (e.g., a keyboard, one or more buttons, a camera, a microphone, or a touchpad).

Monitor 14 and display monitor 26 may communicate utilizing any suitable transmission medium, including wireless (e.g., WiFi, Bluetooth, etc.), wired (e.g., USB, Ethernet, etc.), or application-specific connections. In an exemplary embodiment, monitor 14 and display monitor 26 may be connected via cable 32. Monitor 14 and display monitor 26 may communicate utilizing standard or proprietary communications protocols, such as the Standard Host Interface Protocol (SHIP) developed and used by Covidien of Mansfield, Mass. In addition, monitor 14, display monitor 26, or both may be coupled to a network to enable the sharing of information with servers or other workstations (not shown). Monitor 14, display monitor 26, or both may be powered by a battery (not shown) or by a conventional power source such as a wall outlet.

Monitor 14 may transmit calculated physiological parameters (e.g., pulse rate, blood oxygen saturation, and respiration information) to display monitor 26. In some embodiments, monitor 14 may transmit a PPG signal, data representing a PPG signal, or both to display monitor 26, such that some or all calculated physiological parameters (e.g., pulse rate, blood oxygen saturation, and respiration information) may be calculated at display monitor 26. In an exemplary embodiment, monitor 14 may calculate pulse rate and blood oxygen saturation, while display monitor 26 may calculate respiration information such as a respiration rate.

Figure 2:
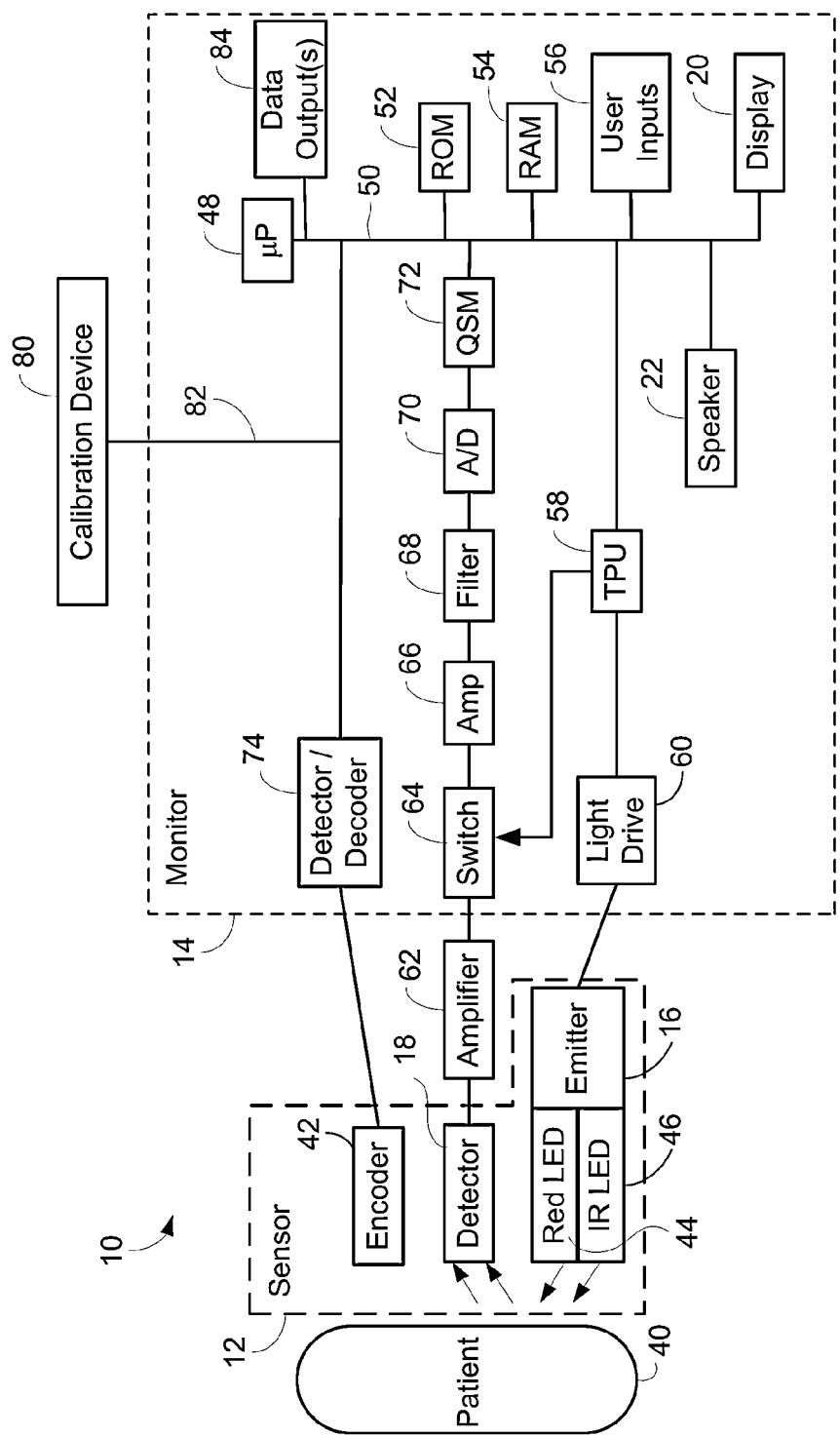
FIG. 2 is a block diagram of the illustrative patient monitoring system of FIG. 1 coupled to a patient in accordance with some embodiments of the present disclosure.

FIG. 2 is a block diagram of a patient monitoring system, such as patient monitoring system 10 of FIG. 1, which may be coupled to a patient 40 in accordance with an embodiment. Certain illustrative components of sensor unit 12 and monitor 14 are illustrated in FIG. 2.

Sensor unit 12 may include emitter 16, detector 18, and encoder 42. In the embodiment shown, emitter 16 may be configured to emit at least two wavelengths of light (e.g., Red and IR) into a patient's tissue 40. Hence, emitter 16 may include a Red light emitting light source such as Red light emitting diode (LED) 44 and an IR light emitting light source such as IR LED 46 for emitting light into the patient's tissue 40 at the wavelengths used to calculate the patient's physiological parameters. In some embodiments, the Red wavelength may be between about 600 nm and about 700 nm, and the IR wavelength may be between about 800 nm and about 1000 nm. In embodiments where a sensor array is used in place of a single sensor, each sensor may be configured to emit a single wavelength. For example, a first sensor may emit only a Red light while a second sensor may emit only an IR light. In a further example, the wavelengths of light used may be selected based on the specific location of the sensor.

It will be understood that, as used herein, the term "light" may refer to energy produced by radiation sources and may include one or more of radio, microwave, millimeter wave, infrared, visible, ultraviolet, gamma ray or X-ray electromagnetic radiation. As used herein, light may also include electromagnetic radiation having any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In some embodiments, detector 18 may be configured to detect the intensity of light at the Red and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the Red and IR wavelengths in the patient's tissue 40.

In some embodiments, encoder 42 may contain information about sensor unit 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which measurements may be determined based at least in part on the signal or signals received at sensor unit 12. For example, some pulse oximetry sensors rely on equations to relate an area under a portion of a PPG signal corresponding to a physiological pulse to determine blood pressure. These equations may contain coefficients that depend upon a patient's physiological characteristics as stored in encoder 42. Encoder 42 may, for instance, be a coded resistor that stores values corresponding to the type of sensor unit 12 or the type of each sensor in the sensor array, the wavelengths of light emitted by emitter 16 on each sensor of the sensor array, and/or the patient's characteristics. In some embodiments, encoder 42 may include a memory on which one or more of the following information may be stored for communication to monitor 14; the type of the sensor unit 12; the wavelengths of light emitted by emitter 16; the particular wavelength each sensor in the sensor array is monitoring; a signal threshold for each sensor in the sensor array; any other suitable information; or any combination thereof.

In some embodiments, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, data output 84, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium that can be used to store the desired information and that can be accessed by components of the system.

In the embodiment shown, a time processing unit (TPU) 58 may provide timing control signals to light drive circuitry 60, which may control when emitter 16 is illuminated and multiplexed timing for Red LED 44 and IR LED 46. TPU 58 may also control the gating-in of signals from detector 18 through amplifier 62 and switching circuit 64. These signals are sampled at the proper time, depending upon which light source is illuminated. The received signal from detector 18 may be passed through amplifier 66, low pass filter 68, and analog-to-digital converter 70. The digital data may then be stored in a queued serial module (QSM) 72 (or buffer) for later downloading to RAM 54 as QSM 72 is filled. In some embodiments, there may be multiple separate parallel paths having components equivalent to amplifier 66, filter 68, and/or A/D converter 70 for multiple light wavelengths or spectra received. Any suitable combination of components (e.g., microprocessor 48, RAM 54, analog to digital converter 70, any other suitable component shown or not shown in FIG. 2) coupled by bus 50 or otherwise coupled (e.g., via an external bus), may be referred to as "processing equipment."

In some embodiments, microprocessor 48 may determine the patient's physiological parameters, such as $SpO_2$, pulse rate, and/or respiration information, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to decoder 74. These signals may include, for example, encoded information relating to patient characteristics. Decoder 74 may translate these signals to enable the microprocessor to determine the thresholds based at least in part on algorithms or look-up tables stored in ROM 52. In some embodiments, user inputs 56 may be used to enter information, select one or more options, provide a response, input settings, any other suitable inputting function, or any combination thereof. User inputs 56 may be used to enter information about the patient, such as age, weight, height, diagnosis, medications, treatments, and so forth. In some embodiments, display 20 may exhibit a list of values, which may generally apply to the patient, such as, for example, age ranges or medication families, which the user may select using user inputs 56.

Calibration device 80, which may be powered by monitor 14 via a communicative coupling 82, a battery, or by a conventional power source such as a wall outlet, may include any suitable signal calibration device. Calibration device 80 may be communicatively coupled to monitor 14 via communicative coupling 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system).

Data output 84 may provide for communications with other devices such as display monitor 26 utilizing any suitable transmission medium, including wireless (e.g., WiFi, Bluetooth, etc.), wired (e.g., USB, Ethernet, etc.), or application-specific connections. Data output 84 may receive messages to be transmitted from microprocessor 48 via bus 50. Exemplary messages to be sent in an embodiment described herein may include PPG signals to be transmitted to display monitor module 26.

The optical signal attenuated by the tissue of patient 40 can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. Also, because blood is a fluid, it responds differently than the surrounding tissue to inertial effects, which may result in momentary changes in volume at the point to which the oximeter probe is attached.

Noise (e.g., from patient movement) can degrade a sensor signal relied upon by a care provider, without the care provider's awareness. This is especially true if the monitoring of the patient is remote, the motion is too small to be observed, or the care provider is watching the instrument or other parts of the patient, and not the sensor site. Processing sensor signals (e.g., PPG signals) may involve operations that reduce the amount of noise present in the signals, control the amount of noise present in the signal, or otherwise identify noise components in order to prevent them from affecting measurements of physiological parameters derived from the sensor signals.

Figure 3:
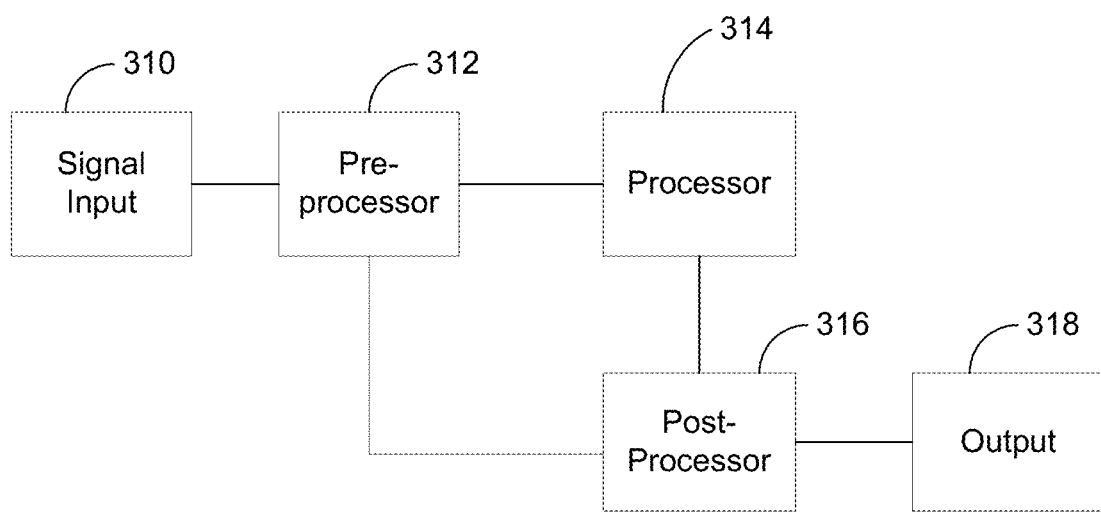
FIG. 3 shows a block diagram of an illustrative signal processing system in accordance with some embodiments of the present disclosure.

FIG. 3 is an illustrative processing system 300 in accordance with an embodiment that may implement the signal processing techniques described herein. In some embodiments, processing system 300 may be included in a patient monitoring system (e.g., patient monitoring system 10 of FIGS. 1-2). Processing system 300 may include input signal 310, pre-processor 312, processor 314, post-processor 316, and output 318. Pre-processor 312, processor 314, and post-processor 316 may be any suitable software, firmware, hardware, or combination thereof for calculating physiological parameters such as respiration information based on input signal 310. For example, pre-processor 312, processor 314, and post-processor 316 may include one or more hardware processors (e.g., integrated circuits), one or more software modules, computer-readable media such as memory, firmware, or any combination thereof. Pre-processor 312, processor 314, and post-processor 316 may, for example, be a computer or may be one or more chips (i.e., integrated circuits). Pre-processor 312, processor 314, and post-processor 316 may, for example, include an assembly of analog electronic components.

In some embodiments, processing system 300 may be included in monitor 14 and/or display monitor 26 of a patient monitoring system (e.g., patient monitoring system 10 of FIGS. 1-2). In the illustrated embodiment, input signal 310 may be a PPG signal. Input signal 310 may be a PPG signal that was sampled and generated at monitor 14, for example at 76 Hz. Input signal 310, pre-processor 312, processor 314, and post-processor 316 may reside entirely within a single device (e.g., monitor 14 or display monitor 26) or may reside in multiple devices (e.g., monitor 14 and display monitor 26).

Input signal 310 may be coupled to pre-processor 312. In some embodiments, input signal 310 may include PPG signals corresponding to one or more light frequencies, such as a Red PPG signal and an IR PPG signal. In some embodiments, the signal may include signals measured at one or more sites on a patient's body, for example, a patient's finger, toe, ear, arm, or any other body site. In some embodiments, signal 310 may include multiple types of signals (e.g., one or more of an ECG signal, an EEG signal, an acoustic signal, an optical signal, a signal representing a blood pressure, and a signal representing a heart rate). The signal may be any suitable biosignal or signals, such as, for example, electrocardiogram, electroencephalogram, electrogastrogram, electromyogram, heart rate signals, pathological sounds, ultrasound, or any other suitable biosignal. The systems and techniques described herein are also applicable to any dynamic signals, non-destructive testing signals, condition monitoring signals, fluid signals, geophysical signals, astronomical signals, electrical signals, financial signals including financial indices, sound and speech signals, chemical signals, meteorological signals including climate signals, any other suitable signal, and/or any combination thereof.

Pre-processor 312 may be implemented by any suitable combination of hardware and software. In an embodiment, pre-processor 312 may be any suitable signal processing device and the signal received from input signal 310 may include one or more PPG signals. An exemplary received PPG signal may be received in a streaming fashion, or may be received on a periodic basis as a sampling window (e.g., every 5 seconds). The received signal may include the PPG signal as well as other information related to the PPG signal (e.g., a pulse found indicator, the mean pulse rate from the PPG signal, the most recent pulse rate estimate, an indicator of invalid samples, and an indicator of artifacts within the PPG signal). It will be understood that input signal 310 may include any suitable signal source, signal generating data, signal generating equipment, or any combination thereof to be provided to pre-processor 312. The signal received at input signal 310 may be a single signal, or may be multiple signals transmitted over a single pathway or multiple pathways.

Pre-processor 312 may apply one or more signal processing operations to input signal 310. For example, pre-processor 312 may apply a pre-determined set of processing operations to input signal 310 to produce a signal that may be appropriately analyzed and interpreted by processor 314, post-processor 316, or both. Pre-processor 312 may perform any necessary operations to provide a signal that may be used as an input for processor 314 and post-processor 316 to determine physiological information such as respiration information. Examples include reshaping the signal for transmission, multiplexing the signal, modulating the signal onto carrier signals, compressing the signal, encoding the signal, filtering the signal, low-pass filtering, band-pass filtering, signal interpolation, downsampling of a signal, attenuating the signal, adaptive filtering, closed-loop filtering, any other suitable filtering, and/or any combination thereof. One example output of operations performed by pre-processor 312 may be to define a set of fiducial points that may be used a baseline to analyze the PPG signal (e.g., to determine respiration information).

Other signal processing operations may be performed by pre-processor 312 for each pulse and may be related to producing morphology metrics suitable as inputs to determine physiological information. Pre-processor 312 may perform calculations based on an analysis window of a series of recently received PPG signal sampling windows (e.g., a 45-second analysis window may correspond to the 9 most recent 5-second sampling windows). The physiological information may be respiration information, which may include any information relating to respiration (e.g., respiration rate, change in respiration rate, breathing intensity, etc.). Because respiration has an impact on pulse characteristics, it may be possible to determine respiration information from a PPG signal. Morphology metrics may be parameters that may be calculated from the PPG signal that provide information related to respiration. Examples include a down metric for a pulse, kurtosis for a pulse, the delta of the second derivative between predetermined samples of consecutive pulses, the up metric for a pulse, skew, ratio of predetermined samples of a pulse or its first or second derivative (e.g., b/a ratio or c/a ratio), peak amplitude of a pulse, center of gravity of a pulse, or area of a pulse, as described in more detail herein. Other information that may be determined by pre-processor 312 may include the pulse rate, the variability of the period of the PPG signal, the variability of the amplitude of the PPG signal, and an age measurement indicative of the age of the useful portion of the analyzed PPG signal.

In some embodiments, pre-processor 312 may be coupled to processor 314 and post-processor 316. Processor 314 and post-processor 316 may be implemented by any suitable combination of hardware and software. Processor 314 may receive physiological information and calculated parameters from pre-processor 312. For example, processor 314 may receive morphology metrics for use in calculating morphology metric signals that may be used to determine respiration information, as well as pulse rate and an age for the morphology metric signals. For example, processor 314 may receive samples representing a number of morphology metric values, such as down metric calculations, kurtosis metric calculations, delta of the second derivative (DSD) metric calculations, and b/a ratio calculations from pre-processor 312. The down metric is the difference between a first (e.g., fiducial) sample of a fiducial-defined portion of the PPG signal and a minimum sample of the fiducial-defined portion of the PPG signal. The DSD metric is the delta (difference) between fiducial points in consecutive fiducial-defined portions of the second derivative of the PPG signal.

Figure 4:
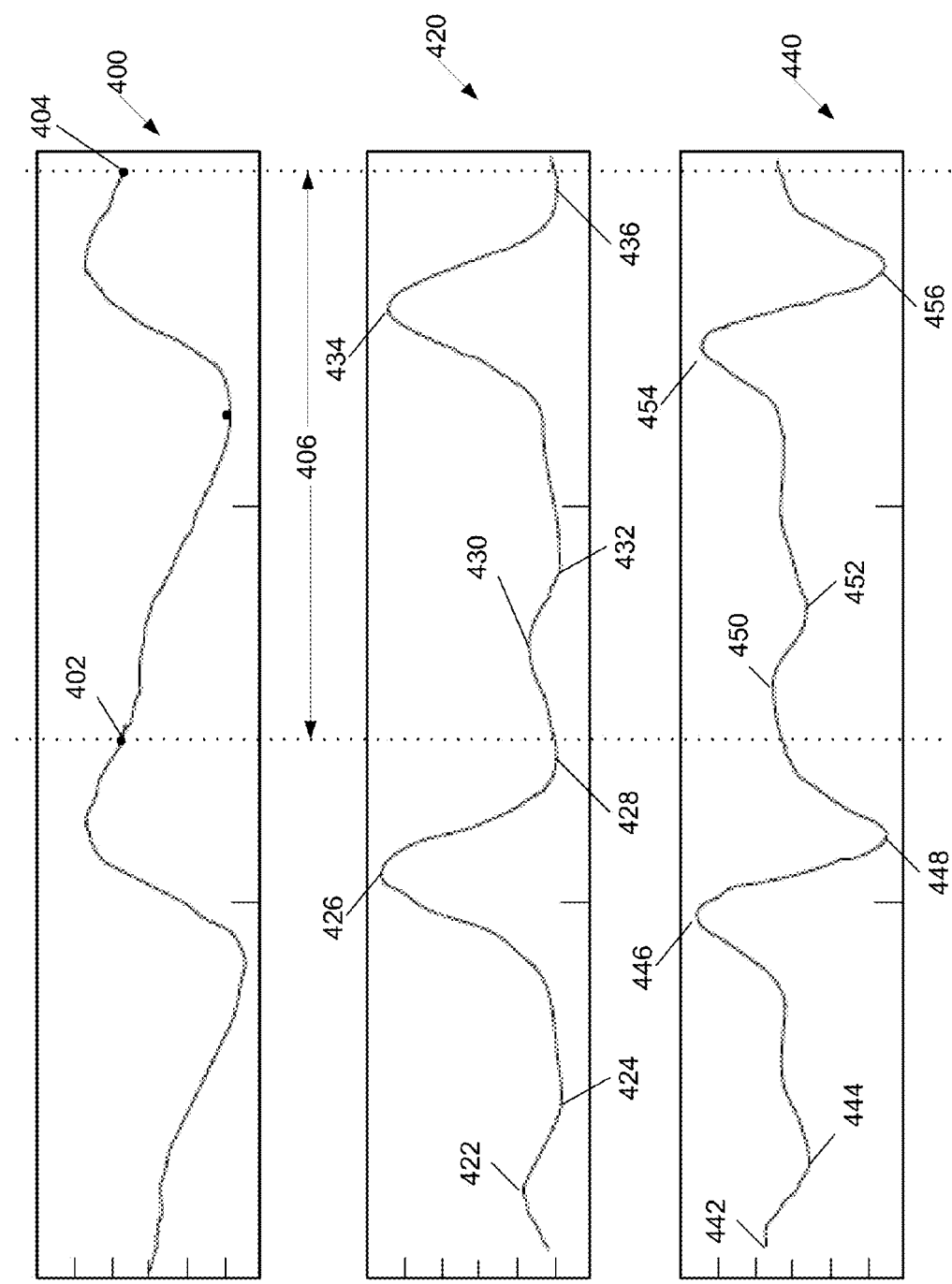
FIG. 4 shows an illustrative PPG signal, a first derivative of the PPG signal, and a second derivative of the PPG signal in accordance with some embodiments of the present disclosure.

The b/a ratio metric (i.e., b/a) is depicted in FIG. 4. FIG. 4 depicts an exemplary PPG signal 400, first derivative of the PPG signal 420, and second derivative of the PPG signal 440. The b/a ratio is based on the ratio between the a-peak and b-peak of the PPG signal 400, first derivative signal 420, or second derivative signal 440. In FIG. 4, the b/a ratio is depicted for the first derivative signal 420 and second derivative signal 440. Fiducial points 402 and 404 of PPG signal 400 define a fiducial-defined portion 406. Each of PPG signal 400, first derivate signal 420, and second derivative signal 440 may include a number of peaks (e.g., four peaks corresponding to maxima and minima) which may be described as the a-peak, b-peak, c-peak, and d-peak, with the a-peak and c-peak generally corresponding to local maxima within a fiducial-defined portion and the b-peak and d-peak generally corresponding to local minima within a fiducial-defined portion. For example, for first derivative signal 420 the a-peaks are indicated by points 426 and 434, the b-peaks by points 428 and 436, the c-peaks by points 422 and 430, and the d-peaks by points 424 and 432. The b/a ratio measures the ratio of the b-peak (e.g., 428 or 436) and the a-peak (e.g., 426 or 434). For second derivative signal 440 the a-peaks are indicated by points 446 and 454, the b-peaks by points 448 and 456, the c-peaks by points 442 and 450, and the d-peaks by points 444 and 452. The b/a ratio measures the ratio of the b-peak (e.g., 448 or 456) and the a-peak (e.g., 446 or 454).

Kurtosis measures the peakedness of a signal, such as the PPG signal, the first derivative of the PPG signal, or the second derivative of the PPG signal. In an exemplary embodiment, the kurtosis metric may be based on the first derivative of the PPG signal. The kurtosis of a signal may be calculated based on the following formulae:

$$D = \frac{1}{n}\sum_{i=1}^{n}(x'_i - \bar{x}')^2 \tag{14}$$

$$\text{Kurtosis} = \frac{1}{nD^2}\sum_{i=1}^{n}(x'_i - \bar{x}')^4 \tag{15}$$

where:
$x_i'$=ith sample of $1^{st}$ derivative;
$\bar{x}'$=mean of 1st derivative of fiducial-defined portion;
n=set of all samples in the fiducial-defined portion.

Processor 314 may utilize the received morphology metric values to calculate morphology metric signals and then to calculate respiration information signals and values from the morphology metric signals. Processor 314 may be coupled to post-processor 316 and may communicate respiration information to post-processor 316. Processor 314 may also provide other information to post-processor 316 such as the signal age related to the signal used to calculate the respiration information, a time ratio representative of the useful portion of the respiration information signal, or a confidence metric indicative of the strength of the respiration information signals. Pre-processor 312 may also provide information to post-processor 316 such as period variability, amplitude variability, and pulse rate information. Post-processor 316 may utilize the received information to calculate an output respiration information, as well as other information such as the age of the respiration information and status information relating to the respiration information output (e.g., whether a valid output respiration information value is currently available). Post-processor 316 may provide the output information to output 318.

Output 318 may be any suitable output device such as one or more medical devices (e.g., a medical monitor that displays various physiological parameters, a medical alarm, or any other suitable medical device that either displays physiological parameters or uses the output of post-processor 316 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

In some embodiments, all or some of pre-processor 312, processor 314, and/or post-processor 316 may be referred to collectively as processing equipment. For example, processing equipment may be configured to amplify, filter, sample and digitize an input signal 310 and calculate physiological information from the signal.

Pre-processor 312, processor 314, and post-processor 316 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by pre-processor 312, processor 314, and post-processor 316 to, for example, store data relating to input PPG signals, morphology metrics, respiration information, or other information corresponding to physiological monitoring.

It will be understood that system 300 may be incorporated into system 10 (FIGS. 1 and 2) in which, for example, input signal 310 may be generated by sensor unit 12 (FIGS. 1 and 2) and monitor 14 (FIGS. 1 and 2). Pre-processor 312, processor 314, and post-processor 316 may each be located in one of monitor 14 or display monitor 26 (or other devices), and may be split among multiple devices such as monitor 14 or display monitor 26. In some embodiments, portions of system 300 may be configured to be portable. For example, all or part of system 300 may be embedded in a small, compact object carried with or attached to the patient (e.g., a watch, other piece of jewelry, or a smart phone). In some embodiments, a wireless transceiver (not shown) may also be included in system 300 to enable wireless communication with other components of system 10 (FIGS. 1 and 2). As such, system 10 (FIGS. 1 and 2) may be part of a fully portable and continuous patient monitoring solution. In some embodiments, a wireless transceiver (not shown) may also be included in system 300 to enable wireless communication with other components of system 10. For example, communications between one or more of pre-processor 312, processor 314, and post-processor 316 may be over BLUETOOTH, 802.11, WiFi, WiMax, cable, satellite, Infrared, or any other suitable transmission scheme. In some embodiments, a wireless transmission scheme may be used between any communicating components of system 300.

Figure 5:
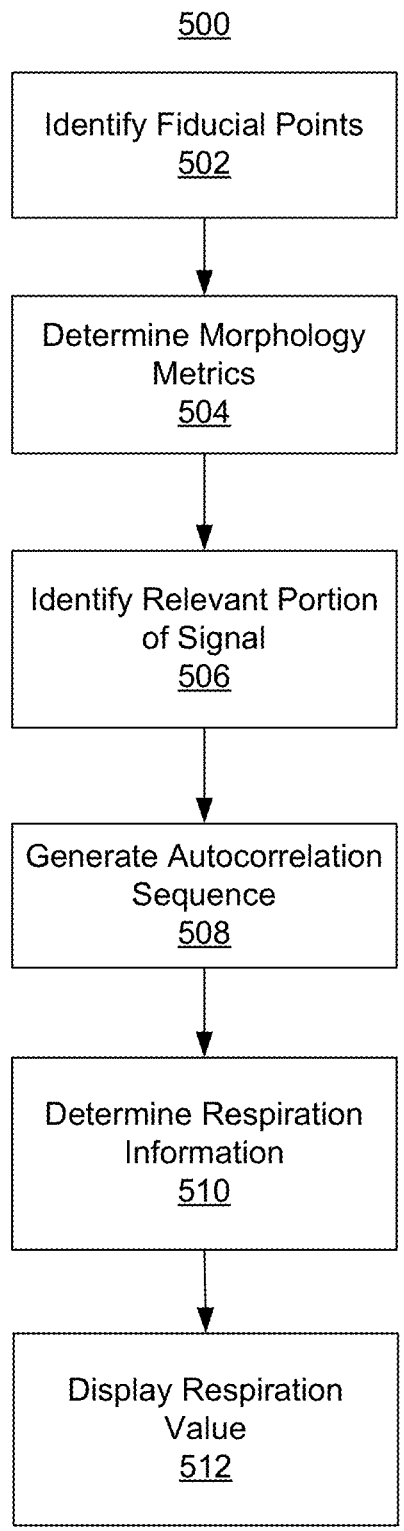
FIG. 5 is a flow diagram showing illustrative steps for determining respiration information from a photoplethysmograph signal in accordance with some embodiments of the present disclosure.

FIG. 5 depicts a flow diagram showing illustrative steps for determining a physiological parameter such as respiration information from a physiological signal such as a PPG signal in accordance with some embodiments of the present disclosure. Although an exemplary embodiment is described herein, it will be understood that each of steps 500 may be performed by pre-processor 312, processor 314, post-processor 316, or any combination thereof. It will also be understood that steps 500 may be performed in alternative sequence or in parallel, that steps may be omitted, and that additional steps may be added or inserted.

At step 502 pre-processor 312 may identify fiducial points for successive pulse waves of a PPG signal. Fiducial points may be identified in any suitable manner. For example, some suitable embodiments for identifying fiducial points are described in detail with respect to FIGS. 6-7 below. The fiducial points may define a series of fiducial-defined portions that may be used as a reference for subsequent calculations (e.g., of morphology metric signals).

At step 504 pre-processor 312 may generate morphology metrics from the PPG signal. Morphology metrics may be calculated from the PPG signal in any suitable manner. In one embodiment, a plurality of morphology metrics may be generated from the PPG signal. Example morphology metrics that may be relevant to determining a physiological parameter such as respiration information from a PPG signal may include a down metric, a kurtosis metric, a delta of second derivative (DSD) metric, an up metric, a skew metric, a ratio of samples metric (e.g., a b/a ratio metric or c/a ratio metric), a i_b metric, a peak amplitude metric, a center of gravity metric, and an area metric. In an exemplary embodiment, morphology metric signals may be generated for the down metric, kurtosis metric, DSD metric, and b/a ratio metric. For each morphology metric a set of morphology metric values, each corresponding to a fiducial defined portion, may be calculated. The sets of morphology metric values may be communicated to processor 314 to be attenuated, interpolated, and filtered to generate the morphology metric signals. Generating morphology metric signals from a PPG signal is described in more detail in co-pending, commonly assigned U.S. patent application Ser. No. 13/243,853, filed Sep. 23, 2011 and entitled "SYSTEMS AND METHODS FOR DETERMINING RESPIRATION INFORMATION FROM A PHOTOPLETHYSMOGRAPH," which is incorporated by reference herein in its entirety.

At step 506, pre-processor 312 may determine a usable portion of the PPG signal. Portions of the received signal may include samples with values that are unlikely to reflect actual values as a result of inaccurate measurement, user error, or other factors. Input signal 310 may be analyzed to identify divergences in the signal baseline, motion artifacts, divergences in pulse period, and any other signal features that may indicate inaccurate measurement, user error, or other factors. Based on this analysis, pre-processor 312 may identify portions of the input signal 310 to be ignored by processor 314 in calculating values such as respiration information. In one embodiment, only those portions of the calculated morphology metric values that correspond to the usable portion of the input signal may be provided to processor 314.

At step 508, processor 314 may generate an autocorrelation sequence from the morphology metric signal. Although an autocorrelation sequence may be generated in any suitable manner, in one embodiment an autocorrelation sequence may be generated for each morphology metric signal and the autocorrelation sequences may be combined into a single autocorrelation sequence based on weighting factors. Generating the autocorrelation sequence from the morphology metric signals is described in more detail in co-pending, commonly assigned U.S. patent application Ser. No. 13/243,951, filed Sep. 23, 2011 and entitled "SYSTEMS AND METHODS FOR DETERMINING RESPIRATION INFORMATION FROM A PHOTOPLETHYSMO-GRAPH," which is incorporated by reference herein in its entirety.

At step 510, processor 314 may determine respiration information based on the autocorrelation sequence. Respiration information may be determined from the autocorrelation sequence in any suitable manner. In one exemplary embodiment, a continuous wavelet transform may be used to determine respiration information such as respiration rate from the autocorrelation sequence, as is described in more detail in in co-pending, commonly assigned U.S. patent application Ser. No. 13/243,892, filed Sep. 23, 2011 and entitled "SYSTEMS AND METHODS FOR DETERMINING RESPIRATION INFORMATION FROM A PHOTOPLETHYSMOGRAPH," which is incorporated by reference herein in its entirety. In another exemplary embodiment, respiration information may be determined directly from the autocorrelation sequence, (e.g., by comparing the peaks of the autocorrelation sequence to a threshold value or by identifying a maximum peak of the autocorrelation sequence within a window of interest). Determining respiration information directly from the autocorrelation sequence is described in more detail in co-pending, commonly assigned U.S. patent application Ser. No. 13/243,785, filed Sep. 23, 2011 and entitled "SYSTEMS AND METHODS FOR DETERMINING RESPIRATION INFORMATION FROM A PHOTOPLETHYSMOGRAPH," which is incorporated by reference herein in its entirety. As is described in more detail herein, the determination of respiration information may be modified based on a historical distribution of respiration values. The output respiration value may be communicated to post-processor 316.

At step 512, post-processor 316 may determine a display respiration value to be displayed (e.g., at the patient monitoring system). The display respiration value may be determined in any suitable manner. For example, the display respiration value may be based on the currently received respiration value. In another exemplary embodiment, the display respiration value may be based on the received respiration value as well as previously received respiration values. In an exemplary embodiment, post-processor 316 may calculate the display respiration value from the respiration value for the current analysis window and respiration values for one or more previous analysis windows, (e.g., the five previous analysis windows).

Figure 6:
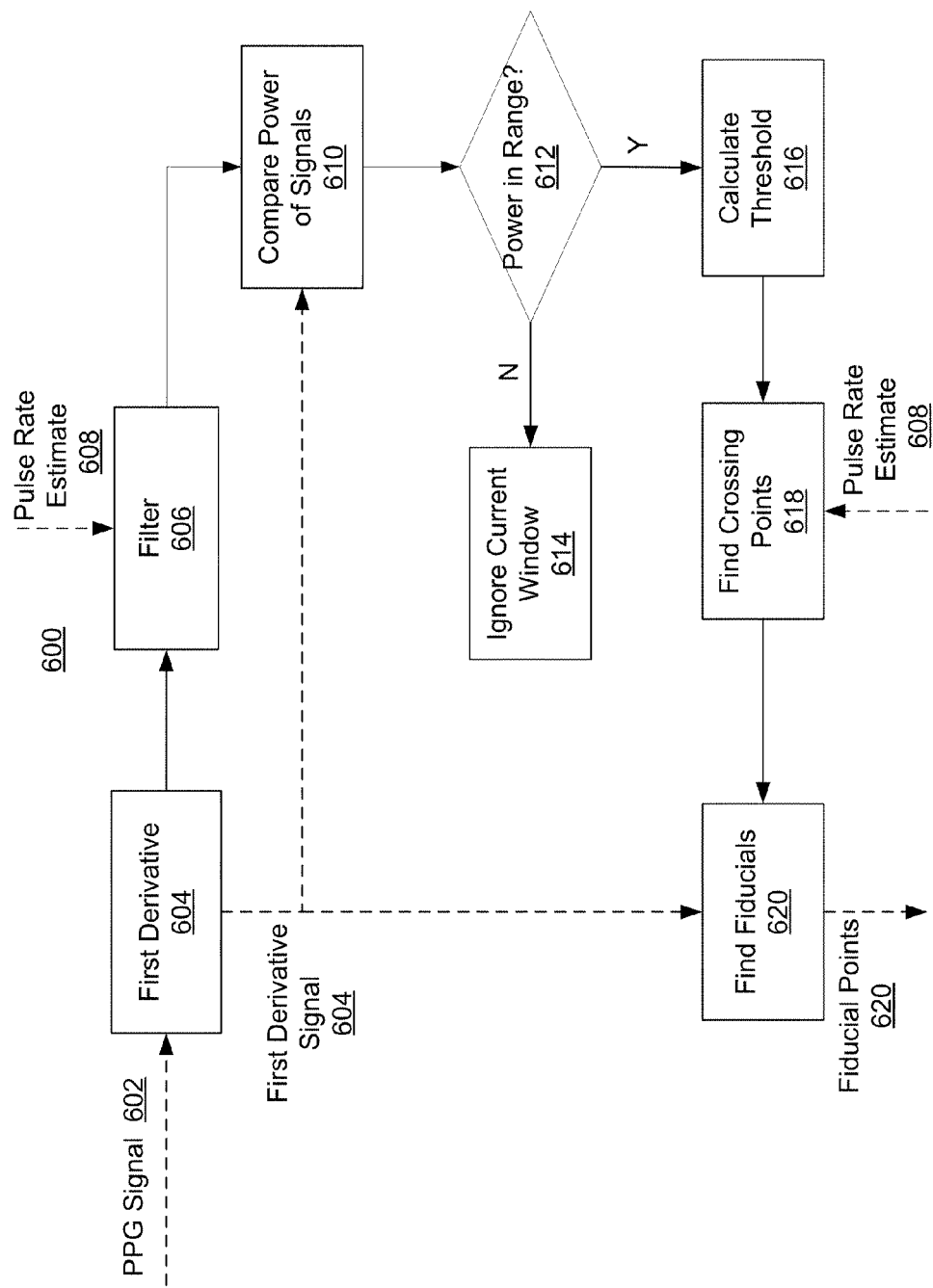
FIG. 6 is a flow diagram showing an illustrative flow for identifying fiducial points from a physiological signal in accordance with some embodiments of the present disclosure.

FIG. 6 depicts an illustrative flow diagram 600 for identifying fiducial points in accordance with an embodiment of the present disclosure. Although in an exemplary embodiment, flow diagram 600 may be executed by pre-processor 312, it will be understood that flow diagram 600 may be executed by processor 314, post-processor 316, or any combination thereof.

Pre-processor 312 may receive an input signal 602. Although in an exemplary embodiment the signal may be a PPG signal 602, it will be understood that input signal 602 may be any signal, including any physiological signal as described herein. In an exemplary embodiment, the received PPG signal 602 may include a sampling window of samples (e.g., a 5-second sampling window of PPG samples sampled at 76 Hz). It will be understood that fiducial points may be determined from any type of received signal, including samples delivered in a streaming fashion.

Figure 7:
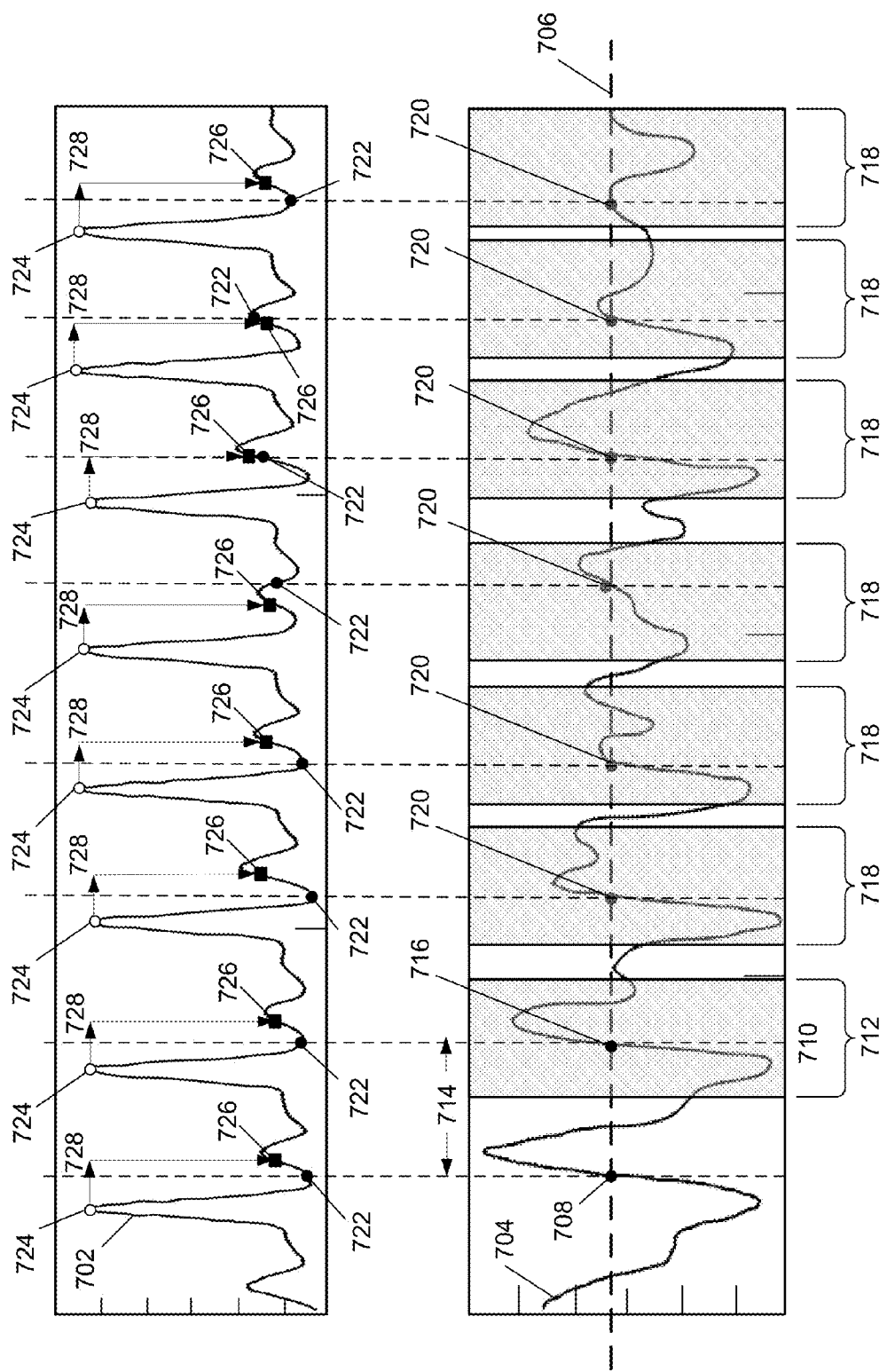
FIG. 7 shows an illustrative first derivative signal of a PPG signal and a filtered first derivative signal in accordance with some embodiments of the present invention.

The flow diagram may continue to step 604, where pre-processor 312 may process PPG signal 602 to assist in determining fiducial points of PPG signal 602. For example, different order signals of PPG signal 602 may provide unique information about PPG signal 602. Although PPG signal 602 may be analyzed without additional processing, or any nth order signal of PPG signal 602 may be used, in an exemplary embodiment a first derivate signal may be determined for PPG signal 602. An exemplary first derivate PPG signal 702 is depicted in FIG. 7.

The flow may continue to step 606, where pre-processor 312 may process the first derivative signal to remove aspects of the signal that are not desirable for identifying fiducial points. The first derivative signal may be processed in any suitable manner (e.g., high-pass filtering, low-pass filtering, band-pass filtering, any other suitable signal processing operation, or any combination thereof). In an exemplary embodiment, the first derivative signal may be band-pass filtered. The band-pass filter may be implemented in any suitable manner, such as elliptical filters, butterworth filters, Chebyshev filters, any other suitable band-pass filter implementation, or any combination thereof. In an exemplary embodiment, the band-pass filter may be implemented with a high-pass second order elliptical filter and a low-pass second order elliptical filter. Although in an exemplary embodiment the first derivative signal may be generated and then filtered, it will be understood that the PPG signal 602 may be processed in any suitable manner. For example, in another embodiment, PPG signal 602 may be band-pass filtered, and the first derivative signal may be generated from the filtered PPG signal 602.

The parameters for the band-pass filter may be fixed or may be variable (e.g., based on characteristics of the PPG signal 602 or a first derivative of PPG signal 602). Although the parameters for the band-pass filter may be determined in any suitable manner, in an exemplary embodiment, the parameters may be based on a pulse rate estimate 608 associated with PPG signal 602. For example, pulse rate estimate 608 may approximate the period of pulse waves within a sampling window, providing a baseline for an appropriate frequency range for the band-pass filter. Although the pass band may be determined in any suitable manner, in an exemplary embodiment the pass band may be based on a predetermined deviation from the pulse rate estimate. In an exemplary embodiment the pass band may be plus or minus 20% of the frequency associated with the pulse rate estimate. An exemplary filtered first derivate PPG signal 704 is depicted in FIG. 7.

It will be understood that the band-pass filter may be implemented in any suitable manner, including in hardware, software, or a combination of hardware and software. In an exemplary embodiment, a set of filter coefficients may be determined for each possible pulse rate estimate. The set of filter coefficients may be stored in a persistent memory table. In another exemplary embodiment, a set of filter coefficients may be estimated in real time for each new pulse rate estimate. Because the filter coefficients may change when the pulse rate changes, it may be desirable to transition between filter settings to limit discontinuities in the output band-pass filtered signal. Although the transition between filter settings may be accomplished in any suitable manner, in an exemplary embodiment one or more previous filter coefficients may be averaged with the current coefficients. The averaging may be weighted to provide additional weight to more recent filter coefficients.

The flow may continue to step 610, where pre-processor 312 may compare the power of the first derivative signal and the filtered first derivative signal (e.g., to determine how much signal energy is located near the pulse rate estimate). Although the power of the signals may be compared in any suitable manner, in an exemplary embodiment a power ratio may be calculated based on the standard deviation of each of the signals:

$$\text{power ratio} = \frac{\text{st\_dev (filtered derivative signal)}}{\text{st\_dev (derivative signal)}} \quad (14)$$

where:
power ratio=the power ratio for the sampling window;
st_dev (filtered derivative signal)=the standard deviation of the filtered first derivative signal;
st_dev (derivative signal)=the standard deviation of the first derivative signal;

The flow may continue to step 612, where pre-processor 312 may determine whether the power ratio is within an acceptable range. Although the power ratio may be analyzed in any suitable manner, in an exemplary embodiment the power ratio may be compared to a predetermined threshold. For example, it may be desirable for the power ratio to exceed a pre-determined threshold, which may indicate that a significant proportion of the signal energy is concentrated near the pulse rate estimate. If the power ratio is not within range, processing may continue to step 614. At step 614, corrective action may be taken based on the power ratio failing to fall within the desired range. Although any suitable corrective action may be taken, in an exemplary embodiment the sampling window may be ignored (i.e., fiducial points may not be identified for the sampling window and no physiological information may be determined for the sampling window). In other embodiments, the sampling window may be flagged with a low confidence indicator when the power ratio is deemed undesirable or outside of a desired range. A sampling window (or an analysis window associated with the sampling window) flagged with a low confidence indicator may be, for example, down-weighted in subsequent processing, such as processing to determine physiological information. In some embodiments, information derived from a sampling window flagged with a low confidence indicator, may be flagged with a low confidence indicator (e.g., a physiological parameter derived from a low confidence sampling window may be presented with a low confidence warning).

In the illustrated embodiment, if the power ratio is within range, the flow may continue to step 616. At step 616, pre-processor 312 may calculate a threshold for determining crossing points. A crossing point may be a point on a signal under analysis that may be useful for identifying fiducial points. Although it will be understood that crossing points may be determined in any suitable manner, in an exemplary embodiment a crossing point may be based on application of a crossing threshold to the filtered first derivative signal. In an exemplary embodiment, the crossing threshold may be based on the power of the filtered first derivative signal. Although it will be understood that the power may be determined in any suitable manner, in an exemplary embodiment, the power may be estimated using the mean absolute deviation of the filtered first derivative signal. Accordingly, the crossing threshold may be based on the mean absolute deviation of the filtered first derivative signal as follows:

$$\text{crossing threshold} = C^* \text{mean}(|x - \text{mean}(x)|) \quad (15)$$

where:
x=the filtered first derivative signal;
mean( )=the mean of a signal;
|x−mean(x)|=absolute value of each sample of the filtered first derivative signal minus the mean of the filtered first derivative signal; and
C=a constant.

Constant value C may be selected in any suitable manner (e.g., based on characteristics of PPG signal 602, of the first derivative of PPG signal 602, of the filtered first derivative signal of PPG signal 602, of any other suitable signal, or any combination thereof). For example, the value of C may be based on an estimate of the signal noise. In an exemplary embodiment, C may be a predetermined value (e.g., 0.65).

The crossing threshold may also be compared to one or more previously calculated crossing threshold values (e.g., the previous 8 crossing threshold values). The power of the filtered first derivative signal, in some embodiments, is not expected to change suddenly. Sudden changes in the power of the signal may be indicative of noise or measurement errors in the underlying PPG signal. Accordingly, if the current crossing threshold deviates significantly from the previous crossing thresholds, it may be desirable to modify the current crossing threshold or ignore the data for the current sampling window.

Although the current crossing threshold may be compared to one or more previous crossing thresholds in any suitable manner, in an exemplary embodiment, the current crossing threshold may be compared to the median value of the previous 8 (or any other suitable number) crossing thresholds. If the current crossing threshold exceeds the median crossing threshold by more than a predetermined amount (e.g., 2 times the median threshold), the current crossing threshold may be modified to account for the possibility of noise in the signal. When the current threshold exceeds the median crossing threshold in whatever manner is implemented (e.g., by being more than 2 times the median threshold), then, in an exemplary embodiment, the current crossing threshold may be increased by a predetermined amount (e.g., to 1.5 times the calculated current crossing threshold value). In some embodiments, if the current crossing threshold does not exceed 2 times the median threshold (or by any other suitable criteria), the current crossing threshold may be used as the crossing threshold value.

Following the calculation of the threshold, the flow may continue to step 618, where pre-processor 312 may locate crossing points based on the crossing threshold. Although it will be understood that crossing points may be determined in any suitable manner, in an exemplary embodiment, the crossing points may be determined by applying the crossing threshold to the filtered first derivative of the PPG signal 602. Referring to FIG. 7, the filtered first derivative signal 704 may be represent a sampling window of data, and crossing threshold 706 may indicate a crossing threshold determined as described herein.

Although it will be recognized that crossing points may be located in any suitable manner, in an exemplary embodiment, a search window may be established. Establishing search windows may prevent the selection of erroneous crossing points (e.g., when signal noise is present). In an exemplary embodiment, a search window may be based on pulse rate estimate 608. Referring to FIG. 7, a first crossing point may be established, (e.g., at crossing point 708). In an exemplary embodiment, first crossing point 708 may correspond to the first sample on the up slope of the filtered first derivative signal 704 that exceeds crossing threshold 706.

Additional crossing points may be located based in part on pulse rate estimate 608. For example, a pulse period estimate may be determined from pulse rate estimate 608. The pulse period estimate may establish a center for a search window (e.g., by adding the pulse period estimate to the previous crossing point value). Although it will be understood that the width and location of the search window may be determined in any suitable manner, in an exemplary embodiment the search window may have a fixed width of 1.2 times the pulse rate estimate (depicted as 712) and be centered at 1 times the estimated pulse period (based on estimated pulse period 714) from the previous crossing point.

Once the search window 712 is established, a next crossing point may be determined. In an exemplary embodiment, analysis may start from the first point or sample of filtered first derivative signal 704 within search window 712. The first point that exceeds crossing threshold 706 may be the next crossing point 716. For example, any subsequent point that exceeds crossing threshold 706 within the search window 712 may be ignored. Once a crossing point is established for search window 712, the process may be repeated, establishing each subsequent search window 718 and crossing point 720 for the sampling window. Although it will be recognized that crossing points 720 may be located in any suitable manner, in an exemplary embodiment the search process may be implemented as illustrated in the following pseudo-code:

```
first_point = first threshold crossing after initialization
current_point = first_point
search_window_start = current point + .4 * pulse_period
    estimate
length_of_window = 5 seconds of samples
while (search_window_start < length_of_window)
    search_window_end = min(length_of_window,
        current_point + 1.6*pulse_period_estimate)
    find the first point in between search_window_start
        and search_window_end that crosses the threshold
        on an upslope
    if (crossing point found)
        add point to the set of crossing point
        search_window_start = location of crossing point +
            .4*pulse_period_estimate
    else
        search_window_start = search_window_end+1
    end
end
```

In another embodiment, crossing points may be located based on the crossing threshold without use of the search window. In this embodiment, a crossing point may be established at each point where the filtered first derivative signal 704 exceeds the crossing threshold on an up slope. The crossing points may then be validated by use of any suitable criteria. In an exemplary embodiment, if any consecutive crossing points occur within less than a predetermined percentage of the pulse period, one or both of the consecutive crossing points may be discarded. Although the predetermined threshold may be determined in any suitable manner, in an exemplary embodiment the predetermined threshold may be 25% of the pulse period. Although the decision of which of the consecutive crossing points to discard may be made in any suitable manner, in an exemplary embodiment the crossing point that is closest to another adjacent crossing point may be discarded.

When crossing points are established at step 618, pre-processor 312 may establish fiducial points at step 620. In an exemplary embodiment, the crossing points may be translated to the first derivative signal 702. As is depicted in FIG. 7, translated points 722 may be determined for first derivative signal 702. Translated points may be established in any suitable manner for any suitable signal, such as by translating crossing points to PPG signal 602 or to a second derivative signal of PPG signal 602. In an exemplary embodiment, the translated points may correspond to the location of the crossing points.

In an exemplary embodiment, a maximum point 724 of the first derivative signal 702 may be determined for the region between each consecutive set of translated points 722. Fiducial points 726 may then be established from the maximum points 724 in any suitable manner (e.g., based on a predetermined delay 728). In an exemplary embodiment, PPG signal 602 may be sampled at 76 Hz, and the predetermined delay may correspond to 16 samples or approximately 0.21 seconds. It will be understood that the predetermined delay may be any suitable fixed delay (e.g., as determined based on an empirical analysis). In another embodiment, the delay could be variable instead of predetermined, (e.g., based on characteristics of PPG signal 602 or first derivative signal 702, or based on pulse rate estimate 608). For example, the delay may be a function of the pulse rate estimate, and may increase linearly with the pulse period estimate.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:

1. A method for determining respiration rate information from a photoplethysmograph (PPG) signal, the method comprising:
   receiving, at processing equipment, the PPG signal from a PPG sensor;
   generating, using the processing equipment, a derivative signal from the PPG signal;
   establishing, using the processing equipment, a pass band for a band-pass filter, wherein the establishing the pass band for the pass band filter comprises:
      receiving a pulse rate estimate signal, and
      establishing, using the processing equipment, a low pass cut off value and a high pass cut off value based at least in part on the pulse rate estimate signal;
   filtering, using the processing equipment, the derivative signal based at least in part on the band-pass filter to generate a processed PPG signal;

calculating, using the processing equipment, a crossing threshold based at least in part on the processed PPG signal;

determining, using the processing equipment, a plurality of fiducial points based at least in part on the crossing threshold and based at least in part on at least one of the PPG signal, the derivative signal, a second derivative of the PPG signal, and the processed PPG signal;

determining, using the processing equipment, at least one metric based at least in part on the plurality of fiducial points;

determining, using the processing equipment, the respiration rate information by analyzing the at least one metric; and displaying, on a display device, an output indicative of the respiration rate information.

2. The method of claim 1, wherein determining the plurality of fiducial points comprises:

establishing a search window of the processed PPG signal;

determining a plurality of crossing points of the processed PPG signal based at least in part on the crossing threshold and the search window; and calculating the plurality of fiducial points based on the plurality of crossing points.

3. The method of claim 2, wherein establishing the search window comprises:

establishing the search window based at least in part on the pulse rate estimate signal.

4. The method of claim 2, wherein calculating the plurality of fiducial points comprises:

translating the plurality of crossing points to the derivative signal;

determining a plurality of maximum values, wherein each maximum value comprises a maximum value of the derivative signal between two consecutive crossing points; and calculating the plurality of fiducial points based at least in part on the plurality of maximum values and a delay value.

5. A non-transitory computer-readable medium for use in determining physiological information from a photoplethysmograph (PPG) signal, the computer-readable medium having computer program instructions recorded thereon for:

receiving, at processing equipment, the PPG signal from a PPG sensor; generating, using the processing equipment, a derivative signal from the PPG signal; establishing, using the processing equipment, a pass band for a band-pass filter, wherein the establishing the pass band for the pass band filter comprises: receiving a pulse rate estimate signal, and establishing, using the processing equipment, a low pass cut off value and a high pass cut off value based at least in part on the pulse rate estimate signal;

filtering, using the processing equipment, the derivative signal based at least in part on the band-pass filter to generate a processed PPG signal;

calculating, using the processing equipment, a crossing threshold based at least in part on the processed PPG signal;

determining, using the processing equipment, a plurality of fiducial points based at least in part on the crossing threshold and based at least in part on at least one of the PPG signal, the derivative signal, a second derivative of the PPG signal, and the processed PPG signal;

determining, using the processing equipment, at least one metric based at least in part on the plurality of fiducial points;

determining, using the processing equipment, the respiration rate information by analyzing the at least one metric;

displaying, on a display device, an output indicative of the respiration rate information.

6. The computer-readable medium of claim 5, having further computer program instructions recorded thereon for:

establishing a search window of the processed PPG signal;

determining a plurality of crossing points of the processed PPG signal based at least in part on the crossing threshold and the search window; and calculating the plurality of fiducial points based on the plurality of crossing points.

7. The computer-readable medium of claim 6, having further computer program instructions recorded thereon for:

establishing the search window based at least in part on the pulse rate estimate signal.

8. The computer-readable medium of claim 6, having further computer program instructions recorded thereon for:

translating the plurality of crossing points to the derivative signal;

determining a plurality of maximum values, wherein each maximum value comprises a maximum value of the derivative signal between two consecutive crossing points; and calculating the plurality of fiducial points based at least in part on the plurality of maximum values and a delay value.

9. A patient monitoring system comprising:

an interface configured to receive a photoplethysmograph PPG signal from a PPG sensor; and processing equipment coupled to the interface, the processing equipment configured to: generate a derivative signal from the PPG signal;

establish a pass band for a band-pass filter, wherein to establish the pass band for the pass band filter comprises:

receiving a pulse rate estimate signal, and establishing a low pass cut off value and a high pass cut off value based at least in part on the pulse rate estimate signal;

filter, using the processing equipment, the derivative signal based at least in part on the band-pass filter to generate a processed PPG signal;

calculate a crossing threshold based at least in part on the processed PPG signal;

determine a plurality of fiducial points based at least in part on the crossing threshold and based at least in part on at least one of the PPG signal, the derivative signal, a second derivative of the PPG signal, and the processed PPG signal;

determine, at least one metric based at least in part on the plurality of fiducial points;

determine, the respiration rate information by analyzing the at least one metric; and a display device configured to display an output indicative of the respiration rate information.

10. The patient monitoring system of claim 9, wherein the processing equipment is further configured to:

establish a search window of the processed PPG signal;

determine a plurality of crossing points of the processed PPG signal based at least in part on the crossing threshold and the search window; and calculate the plurality of fiducial points based on the plurality of crossing points.

11. The patient monitoring system of claim 10, wherein the processing equipment is further configured to:
   establish the search window based at least in part on the pulse rate estimate signal.

* * * * *